US010596081B2

(12) United States Patent
Delmas et al.

(10) Patent No.: US 10,596,081 B2
(45) Date of Patent: Mar. 24, 2020

(54) COMPOSITION COMPRISING GELLED CAPSULES STABILIZED BY A BUFFER

(71) Applicant: CAPSUM, Marseilles (FR)

(72) Inventors: Thomas Delmas, Marseilles (FR); Mathieu Goutayer, Saint Malo (FR)

(73) Assignee: CAPSUM, Marseilles (FR)

( * ) Notice: Subject to any disclaimer, the term of this patent is extended or adjusted under 35 U.S.C. 154(b) by 0 days.

(21) Appl. No.: 15/035,822

(22) PCT Filed: Nov. 14, 2014

(86) PCT No.: PCT/EP2014/074663
§ 371 (c)(1),
(2) Date: May 11, 2016

(87) PCT Pub. No.: WO2015/071433
PCT Pub. Date: May 21, 2015

(65) Prior Publication Data
US 2016/0296432 A1    Oct. 13, 2016

(30) Foreign Application Priority Data
Nov. 18, 2013    (FR) ..................................... 13 61311

(51) Int. Cl.
| | |
|---|---|
| *A61K 8/11* | (2006.01) |
| *A61K 8/73* | (2006.01) |
| *A61Q 19/00* | (2006.01) |
| *A61K 9/50* | (2006.01) |
| *A61K 9/10* | (2006.01) |
| *A61K 8/55* | (2006.01) |
| *A61K 8/40* | (2006.01) |
| *A61K 8/49* | (2006.01) |
| *A61K 8/20* | (2006.01) |
| *A61K 8/92* | (2006.01) |

(52) U.S. Cl.
CPC .................. *A61K 8/11* (2013.01); *A61K 8/20* (2013.01); *A61K 8/40* (2013.01); *A61K 8/49* (2013.01); *A61K 8/494* (2013.01); *A61K 8/55* (2013.01); *A61K 8/733* (2013.01); *A61K 8/922* (2013.01); *A61K 9/10* (2013.01); *A61K 9/5036* (2013.01); *A61K 9/5089* (2013.01); *A61Q 19/00* (2013.01); *A61K 2800/805* (2013.01)

(58) Field of Classification Search
CPC ...... A61K 2800/805; A61K 8/11; A61K 8/20; A61K 8/40; A61K 8/49; A61K 8/494; A61K 8/55; A61K 8/733; A61K 8/922; A61K 9/10; A61K 9/5036; A61K 9/5089; A61Q 19/00
See application file for complete search history.

(56) References Cited

U.S. PATENT DOCUMENTS

| | | | | |
|---|---|---|---|---|
| 4,923,645 A | * | 5/1990 | Tsang ................... | A61K 9/1652 264/4.3 |
| 5,286,495 A | * | 2/1994 | Batich .................. | A61K 9/1652 424/488 |
| 5,459,054 A | * | 10/1995 | Skjak-Braek ........ | A61K 9/1652 424/422 |
| 5,593,680 A | * | 1/1997 | Bara ..................... | A61K 8/0212 424/401 |
| 5,883,085 A | * | 3/1999 | Blank .................. | A61K 8/0208 424/400 |
| 2003/0175517 A1 | * | 9/2003 | Voigt ................... | A61K 9/5026 428/402.2 |
| 2007/0275080 A1 | * | 11/2007 | Laulicht .................. | B01J 13/08 424/493 |
| 2012/0003285 A1 | * | 1/2012 | Bibette ................ | A61K 9/4816 424/401 |

FOREIGN PATENT DOCUMENTS

FR          2 986 165 A1     8/2013

OTHER PUBLICATIONS

Aslani et al. (Journal of Microencapsulation 1996, 13(5), 601-614.*
Augst et al. (Macromolecular Bioscience 2006, 6(8), 623-633.*
Dhoot N O et al.: "Microencapsulated Liposomes in Controlled Drug Delivery: Strategies to Modulate Drug Release and Eliminate the Burst Effect", Journal of Pharmaceutical Sciences, American Pharmaceutical Association, Washington, US, vol. 92, No. 3, Mar. 1, 2003 (Mar. 1, 2003), pp. 679-689, XP001143698, ISSN: 0022-3549, DOI: 10.1002/JPS.19104.
El-Gibaly I et al.: "Development, Characterization and In Vivo Evaluation of Polyelectrolyte Complex Membrane Gel Microcapsules Containing Melatonin-Resin Complex for Oral Use", Bulletin of Pharmaceutical Sciences, Assiut University Press, Assiut, EG, vol. 21, No. 2, Jan. 1, 1998 (Jan. 1, 1998), pp. 117-139, XP008076829, ISSN: 1110-0052.
Liu P et al.: "Alginate-Pectin-Poly-L-Lysine Particulate As a Potential Controlled Release Formulation", Journal of Pharmacy and Pharmacology, John Wiley & Sons Ltd, London; GB, vol. 51, No. 2, Feb. 1, 1999 (Feb. 1, 1999), pp. 141-149, XP009034385, ISSN: 0022-3573, DOI: 10.1211/0022357991772259.
Zhang Y et al.: "Preparation and evaluation of alginate-chitosan microspheres for oral delivery of insulin", European Journal of Pharmaceutics and Biopharmaceutics, Elsevier Science Publishers B. V., Amsterdam, NL, vol. 77, No. 1, Jan. 1, 2011 (Jan. 1, 2011), pp. 11-19, XP027571339, ISSN: 0939-6411.
International Search Report, dated Feb. 26, 2015, from corresponding PCT application.

\* cited by examiner

*Primary Examiner* — Snigdha Maewall
(74) *Attorney, Agent, or Firm* — Young & Thompson

(57) ABSTRACT

A composition includes:
an aqueous composition (A) including a buffer having a pKa between 4.0 and 8.0 and having no more than one carboxylic acid function; and
at least one capsule including a core and a gelled shell including a polyelectrolyte in the gelled state chelated by divalent cations, the shell fully encapsulating the core on the periphery thereof, the capsule being free of eukaryote cells.

13 Claims, No Drawings

COMPOSITION COMPRISING GELLED CAPSULES STABILIZED BY A BUFFER

The present invention concerns a composition comprising gelled capsules.

Capsules of simple or complex structure are known having a polyelectrolyte membrane in the gelled state. These capsules are increasingly being used in the cosmetic and agrifood fields for their ease of use and natural origin. The membrane is composed of natural polyelectrolytes such as alginate, a polysaccharide extracted from brown seaweed, *Laminaria*.

In particular gelled capsules of alginate, carrageenan, gellan, pectin are known.

The principle on which the membranes of these capsules are formed is based on gelling of the polyelectrolyte in the presence of divalent cations such as $Ca^{2+}$ or $Ba^{2+}$ cations for example. With regard to alginate, the alginate chains are composed of two types of statistically sequenced monomers to form the polymer chains: manuronate (M) and guluronate (G). G monomers from 2 isolated chains can join together to form a cage structure in which divalent cations are able to insert themselves for chelation therein. Chelation links are then obtained between chains that were initially isolated and will serve as cross-linkers leading to gelling of the network of alginate chains thereby forming a solid membrane. The gelling principle is the same for carrageenan, gellan or pectin.

Said capsules can be produced using millifluidics allowing the formation of complex structures of drops of liquid in another liquid, the whole being surrounded by a polyelectrolyte membrane to impart solidity and mechanical strength to the system after gelling.

However the polyelectrolyte in the gelled state is in thermodynamic equilibrium between the chelated, gelled form and the isolated, liquid form in solution. Any addition of charged molecules may therefore perturb this equilibrium creating possible new chelating sites for the divalent cations. The polyelectrolyte gel can therefore gradually lose its divalent cations which ensure crosslinking between the polymer chains, translating as return of the gelled polyelectrolyte to its liquid form in solution and hence loss of mechanical strength of the gel.

At the current time there are no means for storing gelled polyelectrolyte capsules allowing their mechanical strength to be maintained over a time of more than one month. For example, a calcium alginate gel placed in pure water will tend spontaneously to return to its liquid form. Therefore alginate gel capsules immersed in pure water gradually lose their mechanical strength and elasticity and finally deteriorate.

There is therefore a need to preserve and stabilise polyelectrolyte gel capsules when they are immersed in an aqueous composition.

The present invention proposes using a buffer to stabilise the mechanical properties of the polyelectrolyte gel capsules.

More specifically, the subject of the present invention is a composition comprising:
- an aqueous composition (A) comprising a buffer having a pKa of between 4.0 to 8.0 and having no more than one carboxylic acid function; and
- at least one capsule comprising a core and a gelled shell comprising a polyelectrolyte in the gelled state chelated by divalent cations, said shell fully encapsulating said core on the periphery thereof, said capsule being free of eukaryote cells.

The composition of the invention typically corresponds to a mixture of the aqueous composition (A) and at least one capsule such as defined above. By « mixture » is meant that the capsule(s) are fully immersed in the aqueous composition (A) and that the gelled shell of the capsules is in contact with the aqueous composition (A). The composition of the invention may comprise one or more additives or one or more active ingredients usually used in the cosmetic field.

The composition of the invention typically corresponds to a suspension of a least one capsule such as defined above in the aqueous composition (A).

It has surprisingly been observed that the use of said buffer allows stabilisation of the mechanical properties of gelled polyelectrolyte capsules immersed in an aqueous composition containing said buffer, for a period of time longer than one month and under temperature conditions possibly ranging from 10° C. to 50° C. More specifically the use of said buffer allows the maintaining of the polyelectrolyte gel in the gelled state and the prevented migration of divalent cations outside the network of polyelectrolyte chains.

The stabilisation of the mechanical properties of the capsules of the composition of the invention can be quantified by measuring the compressive strength (Rc) of capsules which have resided in an aqueous composition (A).

In the present invention the « compressive strength (Rc) » designates the maximum weight that can be withstood by a capsule subjected to a crushing load before rupture by bursting. The compressive strength is expressed herein in grams and corresponds to the weight over and above which the capsule can no longer withstand the crushing load and therefore bursts. A reproducible method for measuring the compressive strength of the capsules according to the invention is described in the examples below. In the present invention a minimum compressive strength of 20 g is required so that capsules of size 2 mm or larger maintain acceptable properties. For capsules having a size of about 5 mm, a minimum compressive strength of 50 g is preferable.

Without wishing to be bound by any particular theory, control over the pH of the aqueous composition (A) in which the gelled polyelectrolyte capsules are immersed allows said stabilisation effect to be obtained.

Under the conditions of implementation of the invention, the buffers of the composition of the invention do not chelate the divalent cations of the polyelectrolyte gel and do not form a precipitate with said cations. In particular, the buffer is not capable of chelating $Ca^{2+}$ cations.

These interactions with the divalent cations would tend to reduce the concentrations of divalent cations free in solution and hence over the long term would cause the divalent cations to migrate from the polyelectrolyte gel to maintain a balance between the cations chelated in the gel and the cations free in solution. This would have the final consequence of loss of gelling of the polyelectrolyte gel and hence complete loss of mechanical strength of the gel.

Buffer

In the present invention by « buffer » is meant a chemical species which, in aqueous solution, maintains the pH of the aqueous composition in which it is solubilised despite the addition of small amounts of an acid or base or despite dilution.

The buffer of the composition of the invention comprises no more than one carboxylic acid function.

Therefore the buffer of the composition of the invention cannot be a dicarboxylic acid (such as malic acid) or tricarboxylic acid (such as citric acid). These compounds are known to destabilise calcium alginate gels (Aslani et al.

Journal of Microencapsulation 1996, 13(5), 601-614 and Augst et al. Macromolecular Bioscience 2006, 6(8), 623-633).

According to one embodiment, the buffer of the composition of the invention does not contain any carboxylic function.

According to one embodiment, the buffer of the composition of the invention comprises one or two sulfonic acid functions, preferably only one.

The pKa of the buffer of the composition of the invention is between 4.0 and 8.0. Preferably the pKa is between 5.0 and 8.0, advantageously between 6.0 and 8.0.

As suitable buffer for implementing the invention a buffer can be used that is selected from the group formed by HEPES, Bis Tris, MES, phosphate buffers, and the mixtures thereof.

HEPES designates 4-(2-hydroxyethyl)-1-piperazine ethane sulfonic acid (CAS No 7365-45-9). HEPES has a pKa of 7.5 and allows an aqueous composition to be buffered over a pH range of 6.8 to 8.2.

Bis Tris designates 2,2-bis(hydroxymethyl)-2,2',2''-nitrilotriethanol (CAS No 6976-37-0). Bis Tris has a pKa of 6.5 and allows an aqueous composition to be buffered over a pH range of 5.8 to 7.2.

MES designates 2-(N-morpholino)ethanesulfonic acid (CAS No 4432-31-9). MES has a pKa of 6.1 and allows an aqueous composition to be buffered over a pH range of 5.5 to 6.7.

In the present invention by «phosphate buffer» is meant a buffer containing dihydrogen phosphate and hydrogen phosphate ions.

A phosphate buffer of the invention can be prepared by dissolving monosodium or monopotassium phosphate and disodium or dipotassium phosphate in water.

As phosphate buffer mention can be made of PBS which designates Phosphate Buffered Saline, prepared by dissolving disodium phosphate (10 mM), monopotassium phosphate (1.76 mM), sodium chloride (137 mM) and potassium chloride (2.7 mM) in water. PBS has a pKa of 7.2 and allows an aqueous composition to be buffered over a pH range of 6.5 to 7.9.

As phosphate buffer mention can also be made of the buffer prepared by dissolving disodium phosphate (0.44 weight %) and monopotassium phosphate (2.74 weight %) in water. Said buffer has a pKa of 5.8.

Preferably HEPES or PBS are used as buffer.

Advantageously HEPES is used.

In general the buffer of the composition of the invention is contained in a concentration of between 10 mM and 300 mM in the aqueous composition (A). According to some embodiments the buffer is contained in a concentration higher than 300 mM, and for example may reach 1000 mM, even 1500 mM.

Preferably the buffer concentration is lower than 250 mM, advantageously lower than 200 mM, more preferably lower than 100 mM.

For example it is possible to use the buffer in a concentration between 20 mM and 150 mM, preferably between 20 mM and 100 mM.

When the buffer is HEPES, it is preferably contained in a concentration between 10 mM and 1000 mM in the aqueous composition (A).

When the buffer is PBS, it is preferably contained in a concentration between 10 mM and 150 mM in the aqueous composition (A).

When the buffer is Bis Tris, it is preferably contained in a concentration between 10 mM and 300 mM in the aqueous composition (A).

When the buffer is MES, it is preferably contained in a concentration between 10 mM and 300 mM in the aqueous composition (A).

Capsules

The composition of the invention may comprise a single capsule or plurality of same or different capsules.

The gelled capsules of the composition of the invention also called «polyelectrolyte gelled capsules» comprise a core and a gelled shell comprising a polyelectrolyte in the gelled state, this shell fully encapsulating said core on the periphery thereof. Preferably the core of the capsules is directly in contact with the gelled shell i.e. there is no intermediate membrane between said core and said shell. The capsules of the invention are necessarily free of eukaryote cells whether in the core or gelled shell thereof or evidently on the outer surface of said shell.

According to one embodiment, the polyelectrolyte gel capsules are alginate gel capsules i.e. the polyelectrolyte is an alginate.

According to one embodiment, the polyelectrolyte gel capsules are alginate gel capsules and the pKa of the buffer of the composition of the invention is between 6.0 and 8.0.

Core

The core of the capsules preferably comprises at least one active ingredient.

For example the liquid core may comprise a single active ingredient or a mixture of several active ingredients.

In the present description, by «active ingredient» is meant a compound having a beneficial physiological effect on the element on which it acts. It is intended for example to protect, maintain in good condition, treat, heal, perfume, flavour or colour.

The active ingredient is advantageously a cosmetic, dermo-pharmaceutical, pharmaceutical, perfuming or food agent.

The core may contain the active ingredient in the form of a pure liquid, or a solution of the active ingredient in a liquid solvent, or a dispersion such as an emulsion or suspension of the active agent in a liquid.

If the active ingredient is a cosmetic agent, it can be selected from among sodium hyaluronate or other hydrating/reparative molecules, vitamins, enzymes, or anti-wrinkle, anti-age, protective/antiradical, antioxidant, soothing, anti-irritant, tautening/smoothing, emollient, slimming, anti-cellulite, firming, modelling, draining, anti-inflammatory, depigmenting, bleaching, self-tanning, exfoliating, cell renewal-stimulating or skin microcirculation-stimulating, UV absorbing or filtering, anti-dandruff active ingredients.

One cosmetic agent able to be contained in the core is cited for example in Council Directive 93/35/ECC dated 14 Jun. 1993. For example this product is a cream, emulsion, lotion, gel and oil for the skin (hands, face, feet etc.), a tinted base (liquid, paste), a bath or shower preparation (salts, foams, oils, gels, etc.), a hair care product (hair dyes and bleaches), a cleansing product (lotions, powders, shampoos), a hair conditioning product (lotions, creams, oils), a hair styling product (lotions, lacquers, brilliantines), shaving product (soaps, foams, lotions, etc.), a product intended to be applied to the lips, sun protection product, a self-tanning product, a skin-whitening product, an anti-wrinkle product.

Dermo-pharmaceutical agents more particularly designate agents acting on the skin.

If the active ingredient is a pharmaceutical agent, it is advantageously selected from among anticoagulants, antithrombogenics, anti-mitotics, anti-proliferation, anti-adhesion, anti-migration agents, cell adhesion promoters, growth factors, antiparasitic molecules, anti-inflammatories, angiogenics, angiogenesis inhibitors, vitamins, hormones, proteins, antifungals, antimicrobial molecules, antiseptics or antibiotics.

If the active ingredient is a perfuming agent it may be in the form of a mixture. Among the perfuming agents particular mention can be made of any type of perfume or fragrance, these terms being used indifferently herein. These perfumes or fragrances are well known to persons skilled in the art and particularly include those mentioned for example in S. Arctander, Perfume and Flavor Chemicals (Montclair, N.J., 1969), S. Arctander, Perfume and Flavor Materials of Natural Origin (Elizabeth, N.J., 1960) and in "Flavor and Fragrance Materials", 1991 (Allured Publishing Co. Wheaton, Ill. USA). The perfumes used in the present invention may comprise natural products such as extracts, essential oils, absolutes, resinoids, resins, solid perfumes, etc. . . . and basic synthesis substances such as hydrocarbons, alcohols, aldehydes, ketones, ethers, acids, esters, acetals, ketals, nitriles, etc. . . . , including saturated and unsaturated compounds, aliphatic, alicyclic and heterocyclic compounds.

Food agents are advantageously vegetable or fruit purees such as mango puree, pear puree, coconut puree, cream of onion, leek, carrot or other preparations able to mix several fruits or vegetables. As a variant they are oils such as a food oil e.g. olive oil, soybean oil, grapeseed oil, sunflower seed oil or any other oil extracted from plants, and food active ingredients such has probiotics, yeasts, vitamins, minerals or oleo-active ingredients.

The core may also comprise a colouring agent.

According to one embodiment, the core is liquid.

According to another embodiment the core is gelled.

When the core is gelled it may contain a polyelectrolyte gel identical to the polyelectrolyte gel of the shell.

Alternatively when the core is gelled it may contain an aqueous solution of a gelling agent different from the polyelectrolyte of the shell. The gelling agent is preferably selected from the group formed by polyosides, galactomannans, polysaccharides, glycosaminoglycans and polyols. Advantageously it is selected from the group formed by xanthan gum, carrageenan, carob, guar gum, Gellan, hyaluronic acid, glycerol, propanediol, cellulose or derivatives thereof.

When a gelling agent is contained in the core it is typically in a concentration of between 0.01% and 1% by weight relative to the total weight of the core.

Shell

The gelled shell of the capsules also called « outer shell » is a gelled membrane comprising a polyelectrolyte in the gelled state chelated by divalent cations which ensure the mechanical strength of the capsules.

The gelled shell can also be called a « membrane » or « skin ».

According to one embodiment the gelled shell has a thickness of less than 500 μm, advantageously thicker than 10 μm, typically between 25 μm and 100 μm.

The gelled shell is generally formed by a monolayer of homogeneous material.

The gelled shell is formed of a hydrogel containing water and a polyelectrolyte chelated by divalent cations, and optionally a surfactant such as described below.

In the present invention the polyelectrolyte contained in the shell of the capsules is a polyelectrolyte reactive to divalent cations.

By « polyelectrolyte reactive to divalent cations » in the meaning of the present invention is meant a polyelectrolyte able to change over from a liquid state in an aqueous solution to a gelled state under the effect of contact with a gelling solution containing divalent cations.

By « divalent cations » is particularly meant cations of alkaline-earth metals selected for example from among calcium ($Ca^{2+}$), barium ($Ba^{2+}$), and magnesium ($Mg^{2+}$) cations. Preferably the divalent cations are calcium cations ($Ca^{2+}$).

The polyelectrolyte may in particular be a natural polysaccharide reactive to multivalent ions such as an alkaline alginate, a gellan, a pectin or a carrageenan.

Preferably the polyelectrolyte is an alginate.

Alginates are produced from brown seaweed called «Laminaria». Such alginates advantageously have a weight content of α-L-guluronate higher than about 50%, preferably higher than 55%, even higher than 60%.

Preferably the polyelectrolyte in the gelled state in the shell of the capsules is calcium alginate.

The individual chains of polyelectrolyte in the liquid state advantageously have a molar mass higher than 65 000 g/moles.

In the gelled state, the individual polyelectrolyte chains together with the divalent cations form a coherent three-dimensional network which retains the liquid core preventing the flowing thereof. The individual chains are retained relative to one another and are unable to flow freely in relation to each other. In this state the viscosity of the formed gel is infinite.

The three-dimensional polyelectrolyte gel contained in the shell traps the water (and surfactant if any). The weight content of polyelectrolyte in the shell is between 0.5 and 5% for example relative to the total weight of the shell.

The gelled shell may also contain a surfactant.

The surfactant is advantageously an anionic surfactant, non-ionic surfactant, cationic surfactant or a mixture thereof. The molecular weight of the surfactant is between 150 g/mol and 10 000 g/mol, advantageously between 250 g/mol and 1 500 g/mol.

If the surfactant is an anionic surfactant it can be selected for example from among alkylsulfates, alkylsulfonates, alkylarylsulfonates, alkaline alkylphosphates, dialkylsulfosuccinates, the alkaline-earth salts of saturated or unsaturated fatty acids. These surfactants advantageously have at least one hydrophobic hydrocarbon chain having a number of carbons higher than 5 even 10, and at least one hydrophilic anionic group such as a sulfate, sulfonate or carbon/late attached to one end of the hydrophobic chain.

If the surfactant is a cationic surfactant, it is selected for example from among the salts of alkylpyridium or alkylammonium halides such as the chloride or bromide of n-ethyldodecylammonium, the chloride or bromide of cetylammonium (CTAB, CTAC). These surfactants advantageously have at least one hydrophobic hydrocarbon chain having a number of carbon atoms higher than 5 even 10, and at least one hydrophilic cationic group such as a quaternary ammonium cation.

If the surfactant is a non-ionic surfactant it is selected for example from among polyoxyethylenated and/or polyoxypropylenated derivatives of fatty alcohols, fatty acids, or alkylphenols, arylphenols, or from among alkylglucosides, polysorbates and cocamides.

According to one embodiment of the invention, the surfactant is sodium laurylsulfate (SLS or SDS).

The weight content of surfactant in the shell is higher than 0.001% and is advantageously lower than 0.1%.

Preferably the capsules are of substantially spherical shape with an outer diameter larger than 0.5 mm, advantageously less than 10 mm and preferably between 1 and 5 mm. They can also be designated as « pearls ».

Advantageously the gelled shell of the complex capsules is such that the volume ratio $R_v$ of core volume to gelled shell volume is higher than 2 and in particular higher than 5. This ratio $R_v$ is advantageously lower than 50. For example it is between 5 and 10.

Several embodiments are possible for the capsules of the composition.

According to one embodiment the core of the capsules contains a proportion of the polyelectrolyte contained in the gelled shell in a concentration however that is lower than the concentration of said polyelectrolyte in the gelled shell. Typically the ratio between the concentration of the polyelectrolyte in the core and the concentration of the polyelectrolyte in the gelled shell is 0.1 or lower, preferably 0.05 or lower.

Preferably the core of the capsules does not contain the polyelectrolyte contained in the gelled shell.

According to one embodiment the capsule is a so-called « simple » capsule meaning that the core is formed of a single inner phase which may be an aqueous or oil phase, said inner phase being placed directly in contact with the gelled shell.

A simple capsule is for example a capsule such as described in international application WO 2010/063937 filed by the Applicant.

A simple capsule therefore comprises two separate phases, an inner phase, preferably liquid, and an outer phase in the gelled state surrounding the inner phase. The active ingredient if any can be contained in the inner phase or in the outer phase. Preferably the active ingredient is contained in the inner phase.

The core of a simple capsule is formed of a single inner phase which may be an aqueous or oil phase.

By « aqueous phase » is meant a phase having the property of solubilising polar, hydrophilic compounds.

An aqueous phase preferably comprises water and at least one active ingredient such as described above which is hydrophilic.

By « oil phase » is meant a phase having the property of solubilising apolar compounds such as fatty substances, oils, lipids.

An oil phase preferably comprises a fatty substance, an oil or a mixture of oils of vegetable, animal or mineral origin.

As vegetable oil, mention can be made of sweet almond oil, jojoba oil, palm oil, argan oil or phytosqualane.

As fatty substance, mention can be made for example of the esters of fatty alcohols and/or fatty acids such as isopropyl myristate, glycerol myristate, isononyl isononanoate, the triglycerides of caprylic acid or capric acid, isopropyl palmitate and ethyl palmitate.

As animal oil, squalene can be cited for example.

As mineral oil, mention can be made for example of hydrogenated polyisobutylene, isododecane, paraffin oils or silicone oils.

According to another embodiment, the capsule is a so-called « complex », capsule meaning that the core comprises a single intermediate drop of an intermediate phase, the intermediate phase being placed directly in contact with the gelled shell, and at least one inner drop of an inner phase arranged in the intermediate phase.

A complex capsule is a capsule such as described for example in international application WO 2012/089820 filed by the Applicant.

The core of a complex capsule may therefore comprise a continuous intermediate phase within which there is a single drop of an inner phase. According to one variant, the core comprises a continuous intermediate phase within which there is a plurality of drops of inner phase(s).

The active ingredient of the core, if any, can be contained in the intermediate phase and/or in the inner phase of the core of the complex capsule.

According to a first variant, the core of a complex capsule comprises an intermediate drop formed of an aqueous intermediate phase and at least one even only one macroscopic inner drop arranged within the intermediate drop and formed of an inner oil phase non-miscible with the aqueous intermediate phase. The term « oil-in-water » core can then be used.

According to another variant, the core of a complex capsule comprises an intermediate drop formed of an intermediate oil phase and at least one even only one inner macroscopic drop arranged within the intermediate drop and formed of an aqueous inner phase non miscible with the intermediate oil phase. The core can then be termed a « water-in-oil » core.

The terms « aqueous phase » and « oil phase » are such as defined above.

The intermediate drop of the core is advantageously liquid. In one variant, the intermediate drop is a thixotropic intermediate phase which is in the liquid state and broken down when it flows but is substantially solid or gelled when at rest.

By « liquid when it flows » is meant that the behaviour of the intermediate phase is viscous i.e. deformation of the material is not only dependent on the stress applied but also on the time during which this stress is applied. One method of characterizing this behaviour is a creep test using a rheometer: a stress characteristic of the flows involved during manufacture is applied to the sample and the strain curve is plotted as a function of time (data obtained with the rheometer software). If the curve has a nonzero slope at long time periods (more than 30 seconds), the intermediate phase can be considered to be liquid. If this slope is zero, the intermediate phase can be considered to be solid.

By « solid or gelled at rest » is meant the behaviour of the intermediate phase that is solid or gelled at rest i.e. the strain exhibited by the material is solely dependent on the stress applied. One method of characterizing this behaviour is a creep test using a rheometer; a stress is applied to the sample characteristic of stresses undergone by the capsule at rest as a function of time (data obtained with the rheometer software). If the curve has a zero slope at long time periods (more than 30 seconds) the intermediate phase can be considered to be solid. If this slope is nonzero the intermediate phase can be considered to be liquid.

Alternatively the intermediate drop is gelled. In this case the intermediate drop is formed for example by gelling a gelling product obtained via change of temperature in particular by a temperature drop of at least 10° C. As a variant, gelling is obtained in the presence of ions, other molecules or certain conditions of pH or ionic strength.

The intermediate drop may comprise one or more active cosmetic, dermo-pharmaceutical, pharmaceutical, perfuming or food ingredients such as defined above.

The intermediate drop may also comprise excipients such as thickeners or rheology modifiers. For example these thickeners are polymers, cross-polymers, microgels, gums or proteins including polysaccharides, celluloses, polyosides, silicone-based polymers and copolymers, colloidal particles (silica, clay, latex . . . ).

The intermediate drop may comprise solid particles and in particular mother-of-pearl particles.

Advantageously the intermediate drop is fully inserted between the inner drop and the gelled shell. Therefore the entirety of the inner surface of the gelled shell is in contact with the intermediate drop so that the intermediate drop holds the inner drop completely away from the gelled shell.

The inner drop(s) may comprise one or more active cosmetic, dermo-pharmaceutical, pharmaceutical, perfuming or food ingredients such as defined above.

The capsule advantageously comprises a single inner drop arranged in the intermediate drop. The inner drop(s) are generally macroscopic. Therefore the maximum cross dimension of each inner drop given by its diameter when it is spherical, is greater than 150 μm, and in particular it is greater than 300 μm. These dimensions are measured with the method using «Image J» processing software on the basis of an image representing at least seven capsules in an overhead view taken by a digital camera.

The minimum volume of at least one inner drop is therefore 0.5% larger than the volume of the core.

The sum of the volumes of the inner drop or of each inner drop is therefore between 0.5% and 65% of total core volume, in particular between 1% and 55% of total core volume.

Each inner drop is advantageously of spherical shape. As a variant the shape of the inner drop differs from a spherical shape and may be elliptic or lenticular for example.

The inner phase forming the inner drops is substantially immiscible with the intermediate phase forming the intermediate drops.

According to another embodiment, the capsules is a so-called «solid» capsule i.e. the core also comprises a polyelectrolyte in the gelled state chelated by divalent cations, said polyelectrolyte being identical to the polyelectrolyte in the shell.

Typically, the composition of the core and the composition of the shell are identical and form one and the same phase. Said capsules can be prepared simply by the dropwise addition of a composition comprising a polyelectrolyte in solution into a gelling solution comprising divalent cations Aqueous Composition (A)

The aqueous composition (A) in which the capsules of the composition of the invention are immersed may be liquid or gelled.

When gelled the aqueous composition (A) is in the form of an «aqueous gel» i.e. it is a solution comprising water and a gelling agent.

In the present description by «gelling agent» is meant a compound able to impart a gel consistency to a composition.

The gelling agent is preferably selected from the group formed by polyosides, galactomannans, polysaccharides, glycosaminoglycans and polyols.

Advantageously it is selected from the group formed by xanthan gum, carrageenan, carob, guar gum, gellan, hyaluronic acid, glycerol, propanediol, cellulose or its derivatives.

Preferably the viscosity of the aqueous composition (A) is lower than 50 Pa·s such as measured at 25° C., preferably lower than 20 Pa·s. Advantageously the aqueous composition (A) has a viscosity between 2 Pa·s and 15 Pa·s such as measured at 25° C.

Said viscosity of the aqueous gel allows good suspending of the capsules in particular over a time of at least one month at a temperature of 40° C.

According to one variant, the composition (A) does not suspend the capsules i.e. they sediment in the composition (A). For this purpose a composition (A) can be used having viscosity lower than 2 Pa·s.

Advantageously the aqueous gel is transparent for better visualisation of the capsule by the consumer. Its texture is chosen as a function of the texture it is desired to obtain for the composition of the invention.

Viscosity is measure using the following method described in particular in international application WO 2013/132082 filed by the Applicant.

A viscometer of Brookfield type is used with No 05 spindle. About 150 g of solution at 25° C. are placed in a 250 ml beaker having a diameter of about 7 cm so that the height of the volume taken up by the 150 g of solution is sufficient to arrive at the gauge marked on the spindle. The viscometer is set in operation at a rate of 10 rpm and it is waited until the displayed value becomes stable.

Preferably the weight percent of water in the aqueous gel is at least 70%, in particular it is between 70% and 85%, preferably between 70% and 80% relative to the total weight of the composition (A).

The aqueous composition (A) may also comprise a cosmetic, dermo-pharmaceutical, pharmaceutical, perfuming or food ingredient such as defined above.

The aqueous composition (A) may also comprise a preserving agent, colouring agent and/or mother of pearl.

Typically the weight ratio between the aqueous composition (A) and the capsules is between 30:70 to 70:30, preferably between 40:60 and 60:40.

Preparation Method

A further subject of the invention is a method to prepare the composition of the invention, comprising:
  preparing capsules such as defined above; and
  placing said capsules in the presence of an aqueous composition (A) such as defined above.

Capsule preparation method suitable for implementing the invention are described in particular in WO 2010/063937 and WO 2012/089820.

The aqueous composition (A) can be prepared by mixing the different ingredients in water and then adding the buffer.

Use

A further subject of the invention is the use of a buffer having a pKa between 4.0 and 8.0 and comprising no more than one carboxylic acid function to maintain the compressive strength (Rc) of the above-defined capsules above a minimum value of 20 g when they are immersed in an aqueous composition comprising said buffer.

Preferably the pKa of the buffer is between 5.0 and 8.0, advantageously between 6.0 and 8.0.

The buffer may be one of the above-described buffers.

The compressive strength (Rc) is such as defined above.

It has surprisingly been observed that the use of said buffer allows maintaining of the compressive strength (Rc) of alginate gel capsules immersed in an aqueous composition comprising said buffer over a period of more than one month under temperature conditions possibly ranging from 10° C. to 50° C. The maintained compressive strength (Rc) can be accounted for through the stabilisation of the alginate in the gelled state, in particular through inhibited migration outside the alginate chain network of the divalent cations chelating said alginate.

If the buffer is selected from the group formed by HEPES, PBS, Bis Tris or MES, the minimum value of Rc may be 40 g, even 50 g.

If the buffer is HEPES, the minimum Rc value may be 65 g.

Cosmetic Composition

According to one embodiment, the composition of the invention is a cosmetic composition in association with a cosmetically acceptable carrier.

A further subject of the invention is a non-therapeutic, cosmetic treatment method of the skin comprising a step to apply to the skin at least one layer of the composition of the invention.

This method is preferably implemented with a composition comprising capsules the active ingredients of which are non-therapeutic, cosmetic agents.

In particular it may be a cosmetic composition.

A further subject of the invention is the cosmetic use of the previously described cosmetic composition.

The invention will be better understood on reading the following examples that are non-limiting.

EXAMPLES

Example 1—Gelled Calcium Alginate Cube Immersed in Osmosed Water

A cube of sodium alginate was prepared by dissolving sodium alginate (5 g) in 30 mL of calcium chloride solution (10 g/L) contained in a tank.

The gelled cube obtained was then placed in pure water held at around 25° C.

The calcium alginate gel started to weaken after one month at 50° C. and became fully liquid after 3 months at 50° C.

Example 2—Gelled Alginate Capsules Immersed in Osmosed Water

Complex capsules such as defined in the description were prepared conforming to the method described in WO 2012/089820. Their diameter was about 4 mm.

The inner drop was formed of argan oil, the intermediate drop was an aqueous solution and the gelled shell was a hydrogel of calcium alginate.

The composition of the capsules was the following:

|  | Trade name | INCI name | Supplier | % capsules (m/m) |
|---|---|---|---|---|
| Inner drop | argan oil | *Argania spinosa* | olvea | 16.66% |
| Intermediate drop | MilliQ Water | Aqua | — | 63.37% |
|  | Hasocri | Sodium Hyaluronate | Soliance | 0.67% |
|  | Microcare CPH | Chlorphenesine | Thor | 0.17% |
|  | Microcare PE | Phenoxyethanol | Thor | 0.47% |
|  | Microcare PTG | Pentylene glycol | Thor | 2.00% |
| Gelled shell | MilliQ Water | Aqua | — | 15.48% |
|  | protanal lf 200 fts | Algin | soliance | 0.33% |
|  | Microcare CPH | Chlorephenesine | Thor | 0.04% |
|  | Microcare PE | Phenoxyethanol | Thor | 0.12% |
|  | Microcare PTG | Pentylene glycol | Thor | 0.50% |
|  | mother-of-pearl |  | Merck | 0.17% |
|  | Sodium Dodecyl Sulfate | Sodium Lauryl Sulfate | Sigma | 0.02% |

The capsules thus prepared were immersed in pure water held at 50° C.

The mechanical strength of the capsules was measured over time by measuring the compressive strength Rc. This property corresponds to the capability of the capsules to withstand compression.

The principle is to apply a stress at constant rate to a capsule and to measure the force required to rupture the capsule. The method used is the one described in international application WO 2013/132083.

The capsule is placed on scales and stress is applied at constant rate via a syringe plunger filled with a constant flow of oil via a syringe actuator (60 mL/h). The weight displayed on the scales is monitored over time which translates the forces applied through the capsule. Compressive strength Rc, is given by the weight limit achieved before rupture of the capsule. It is given analytically when a drop in weight of more than 1% is observed on the scales.

The Rc (in g) of a sample of capsules is determined by determining the mean and standard deviation associated with Rc measurements of 10 capsules chosen at random from the batch.

Rc results of the capsules as a function of immersion time in water are given in Table 1.

TABLE 1

| Time (days) at 50° C. | 0 | 1 | 5 | 30 | 60 | 90 |
|---|---|---|---|---|---|---|
| Rc (g) | 233 | 141 | 114 | 75 | 48 | 14 |

The calcium alginate gel capsules therefore have a mechanical strength which degrades over time in pure water. A very rapid decrease in Rc is observed over the first few days.

Example 3—Alginate Gel Capsules Immersed in an Aqueous Gel with Adjusted Starting pH Example 2 was reproduced replacing osmosed water by an aqueous gel having a pH initially adjusted via acid/base addition (pH adjusted to 6, 8 or 10).

The composition of the aqueous gel was the following:

| Trade name | INCI name | Supplier | % gel (m/m) |
|---|---|---|---|
| MilliQ Water | Aqua | — | 60.7% |
| rhodicare t | Xanthan gum | Rhodia | 0.50% |

-continued

| Trade name | INCI name | Supplier | % gel (m/m) |
|---|---|---|---|
| Microcare PE | Phenoxyethanol | Thor | 0.80% |
| Microcare PTG | Pentylene glycol | Thor | 2.00% |
| glycerol | Glycerin | Acros | 19.00% |
| zemea | Propanediol | Dupont tate | 7.00% |

Nevertheless, as in Example 2, the alginate gel of the capsules lost it mechanical strength in less than one month (at ambient temperature or at 50° C.), irrespective of initially adjusted pH.

Example 3—Alginate Gel Capsules Immersed in a Buffered Aqueous Gel

Example 2 was reproduced replacing the osmosed water by an aqueous gel comprising a buffer (corresponding to aqueous composition (A) described above) with a buffer concentration in the aqueous gel of 500 mM.

The composition of the aqueous gel was the following:

| Trade name | INCI name | Supplier | % gel (m/m) |
|---|---|---|---|
| MilliQ Water | Aqua | — | (60.7-X)% |
| rhodicare t | Xanthan gum | Rhodia | 0.50% |
| Microcare PE | Phenoxyethanol | Thor | 0.80% |
| Microcare PTG | Pentylene glycol | Thor | 2.00% |
| glycerol | Glycerin | Acros | 19.00% |
| zemea | Propanediol | Dupont tate | 7.00% |
| Buffer | | | X% |

The following buffers were used:

| Usual name | Chemical name | Buffer pH range (pKa) | CAS N° |
|---|---|---|---|
| PBS | Phosphate buffered saline: disodium phosphate (10 mM) monopotassium phosphate (1.76 mM) sodium chloride (137 mM) potassium chloride (2.7 mM) | 6.5-7.9 (7.2) | |
| HEPES | 4-(2-hydroxyethyl)-1-piperazine ethane sulfonic acid | 6.8-8.2 (7.5) | 7365-45-9 |
| MES | 2-(N-morpholino)ethanesulfonic acid | 5.5-6.7 (6.1) | 4432-31-9 |
| Bis Tris | 2,2-bis(hydroxymethyl)-2,2',2''-nitrilotriethanol | 5.8-7.2 (6.5) | 6976-37-0 |
| ACES | N-(2-acetamido)-2-aminoethanesulfonic acid | 6.1-7.5 (6.8) | 7365-82-4 |
| PIPES | 1,4-piperazinediethanesulfonic acid | 6.1-7.5 (6.8) | 5625-37-6 |
| Trizma | 2-amino-2-(hydroxymethyl)-1,3-propanediol | 7.0-9.0 (8.1) | 77-86-1 |
| Citric acid/sodium citrate | Citric acid/sodium citrate | 3.8-5.8 (4.8) | 68-04-2 77-92-9 |

The Trizma buffer (pKa>8) very rapidly led to degradation of the alginate gel and hence to loss of structural and mechanical strength of the capsules. The same phenomenon was observed with citric acid (pKa=4.8) and malic acid (pKa=5.1)

The other buffers PBS, HEPES, MES, ACES, PIPES and Bis Tris did not cause deterioration of the alginate gel and allowed the resistance of the alginate capsules to be maintained over time (for a least one month at 50° C.).

Example 4—Influence of Buffer Concentration

The buffer concentrations were decreased to examine the influence thereof on compressive strength (Rc) of the capsules.

The results are given in Table 2.

TABLE 2

| Buffer (concentration) | Rc (g) [initial Rc = 160 g] |
|---|---|
| Bis Tris (40 mM) | 90[1]; 26[4] |
| MES (20 mM) | 135[1] |
| MES (40 mM) | 125[1]; 23[4] |
| MES (100 mM) | 95[1] |
| PBS (20 mM) | >50[2] |
| HEPES (20 mM) | 135[1] and 105[2] |
| HEPES (50 mM) | 125[1]; 90[3]; 68[4] |
| HEPES (100 mM) | 115[1] and 90[3] |
| HEPES (1000 mM) | >50[3] |

[1]after 45 days at 50° C.
[2]after 60 days at 50° C.
[3]after 90 days at 50° C.
[4]after 135 days at 50° C.

The HEPES, MES and Bis Tris buffers allowed the mechanical strength of the capsules to be preserved even after 135 days.

The invention claimed is:

1. A composition comprising:
   an aqueous composition (A) comprising a buffer having a pKa between 4.0 and 8.0 and having no more than one carboxylic acid function; and
   at least one capsule comprising a core and a gelled shell comprising a polyelectrolyte in the gelled state chelated by divalent cations, said shell fully encapsulating said core on the periphery thereof, said capsule being free of eukaryote cells,
   wherein either the core of the capsules is formed of a single aqueous or oil inner phase, said inner phase being placed in contact with the gelled shell, or the core of the capsules comprises a single intermediate drop of an intermediate phase, the intermediate phase being placed in contact with the gelled shell, and at least one inner drop of an inner phase arranged in the intermediate drop,
   wherein the capsules and the aqueous composition (A) form a mixture, and
   wherein the at least one capsule has a compressive strength (Rc) of at least 20 g.

2. The composition according to claim 1 wherein the buffer is selected from the group consisting of HEPES, Bis Tris, MES, phosphate buffers, and mixtures thereof.

3. The composition according to claim 2 wherein the buffer is HEPES or PBS.

4. The composition according to claim 1 wherein the buffer is contained in a concentration of between 10 mM and 300 mM in the aqueous composition (A).

5. The composition according to claim 1 wherein the polyelectrolyte in the gelled state chelated by divalent cations is calcium alginate.

6. The composition according to claim 1 wherein the core of the capsules comprises a polyelectrolyte in the gelled state chelated by divalent cations, said polyelectrolyte being identical to the polyelectrolyte contained in the shell.

7. The composition according to claim 1 wherein the gelled shell of the capsules also comprises a surfactant.

8. The composition according to claim 1 wherein the viscosity of the aqueous composition (A) is lower than 50 Pa·s such as measured at 25° C.

9. The composition according to claim 1 wherein the weight ratio between the aqueous composition (A) and the capsules is between 30:70 and 70:30.

10. A method to prepare the composition according to claim 1, comprising:

preparing capsules comprising a core and a gelled shell comprising a polyelectrolyte in the gelled state chelated by divalent cations, said shell fully encapsulating said core on the periphery thereof, said capsules being free of eukaryote cells; and placing said capsules in the presence of an aqueous composition (A) comprising a buffer having a pKa between 4.0 and 8.0 and having no more than one carboxylic acid function, wherein the capsules and the aqueous composition (A) form a mixture.

11. A non-therapeutic, cosmetic skin treatment method comprising a step to apply to the skin at least one layer of the composition according to claim 1.

12. A method for maintaining the compressive strength (Rc) of capsules as defined in claim 1 above the minimum compressive strength (Rc) value of g, by immersing said capsules in an aqueous composition comprising a buffer having a pKa between 4.0 and 8.0 and having no more than one carboxylic acid function.

13. The composition according to claim 1, wherein the capsules are immersed in the aqueous composition.

* * * * *